US009149396B2

(12) United States Patent
Stjernholm et al.

(10) Patent No.: US 9,149,396 B2
(45) Date of Patent: Oct. 6, 2015

(54) ABSORBENT ARTICLE WITH EMBOSSED ELASTIC SIDE PANELS

(75) Inventors: Ingrid Stjernholm, Lerum (SE); Eva Vastag, Härryda (SE); Jan Wirén, Kållered (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 518 days.

(21) Appl. No.: 13/381,104

(22) PCT Filed: Jul. 3, 2009

(86) PCT No.: PCT/SE2009/050867
§ 371 (c)(1),
(2), (4) Date: Dec. 28, 2011

(87) PCT Pub. No.: WO2011/002369
PCT Pub. Date: Jan. 6, 2011

(65) Prior Publication Data
US 2012/0116342 A1    May 10, 2012

(51) Int. Cl.
| *A61F 13/15* | (2006.01) |
| *A61F 13/20* | (2006.01) |
| *A61F 13/56* | (2006.01) |
| *A61F 13/49* | (2006.01) |
| *A61F 13/491* | (2006.01) |

(52) U.S. Cl.
CPC ....... *A61F 13/5622* (2013.01); *A61F 13/49014* (2013.01); *A61F 13/4915* (2013.01)

(58) Field of Classification Search
CPC ........... A61F 13/5622; A61F 13/49014; A61F 13/62; A61F 13/58; A61F 13/4963; A61F 13/5512; A61F 13/56; A61F 13/49015; A61F 2013/51078

USPC ................ 604/385.03, 385.04, 386–387, 389
See application file for complete search history.

(56) References Cited

U.S. PATENT DOCUMENTS 5,399,219 A * 3/1995 Roessler et al. ............... 156/259
5,605,735 A   2/1997 Zehner et al.
(Continued)

FOREIGN PATENT DOCUMENTS

EC    000922216-0005    4/2009
EC    000922216-0006    4/2009
(Continued)

OTHER PUBLICATIONS

Office Action dated Apr. 28, 2014, issued in corresponding European patent application No. 09846915.8 (5 pages).
(Continued)

*Primary Examiner* — Michele M Kidwell
(74) *Attorney, Agent, or Firm* — Drinker Biddle & Reath LLP (57) ABSTRACT

An absorbent article including a chassis, a pair of opposed elastic side panels attached to the chassis, and at least one fastening tab adhesively attached to each elastic side panel. The at least one fastening tab has a length in the transverse direction of the article and a width in the longitudinal direction of the article and each elastic side panel is embossed on at least a portion thereof, which is adhesively attached to the respective fastening tab, to form at least one embossed groove extending along at least 30%, preferably at least 40% and more preferably at least 60% of the width of the at least one fastening tab.

9 Claims, 8 Drawing Sheets

(56) References Cited

U.S. PATENT DOCUMENTS

| | | | |
|---|---|---|---|
| 5,681,306 A | 10/1997 | Goulait et al. | |
| 6,336,922 B1 * | 1/2002 | VanGompel et al. | 604/385.3 |
| 6,652,501 B2 * | 11/2003 | Malchow et al. | 604/385.01 |
| 2003/0109844 A1 | 6/2003 | Gibbs | |
| 2004/0082931 A1 * | 4/2004 | Tani | 604/387 |
| 2005/0027279 A1 | 2/2005 | Minato et al. | |
| 2005/0043699 A1 | 2/2005 | Minato | |
| 2006/0287637 A1 * | 12/2006 | Lam et al. | 604/389 |
| 2007/0028430 A1 * | 2/2007 | Ahn | 24/399 |
| 2007/0032766 A1 | 2/2007 | Liu et al. | |

FOREIGN PATENT DOCUMENTS

| | | |
|---|---|---|
| EP | 1 035 818 | 4/2002 |
| JP | 3119443 | 10/2000 |
| JP | 2004-215694 | 8/2004 |
| JP | 2010173346 | 8/2010 |
| WO | WO 03/030775 A2 | 4/2003 |
| WO | 2006/065177 | 6/2006 |
| WO | 2008/143560 | 11/2008 |
| WO | WO 2010/044715 A1 | 4/2010 |

OTHER PUBLICATIONS

Office Action issued in corresponding Russian application No. 2012103610 dated Apr. 12, 2013 (with English translation; 7 pages).

Office Action issued in corresponding Chinese patent application No. 200980160268.9 dated Jun. 5, 2013 (with English translation; 15 pages).

Extended European search report mailed Feb. 13, 2014, issued in corresponding European patent application No. 09846915.8 (5 pages).

* cited by examiner

ABSORBENT ARTICLE WITH EMBOSSED ELASTIC SIDE PANELS

CROSS-REFERENCE TO PRIOR APPLICATION

This application is a §371 National Stage Application of PCT International Application No. PCT/SE2009/050867 filed Jul. 3, 2009, which is incorporated herein in its entirety.

TECHNICAL FIELD

The present disclosure relates to an absorbent article including a pair of opposed elastic side panels attached to a chassis and at least one fastening tab adhesively attached to each elastic side panel. Each elastic side panel is embossed in at least a portion thereof which is adhesively attached to each fastening tab, to form at least one embossed groove extending along at least 30%, preferably at least 40% and more preferably at least 60% of the width (w) of the at least one fastening tab.

BACKGROUND

It is desirable that absorbent articles such as diapers and incontinence guards provide a close and comfortable fit about the wearer during use and absorb bodily exudates, such as urine and/or faeces. Typically, conventional diapers have a front waist portion and a back waist portion which are releasably connected about the waist/hips of the wearer during use by conventional fasteners such as adhesive tape fasteners or hook and loop type fasteners. For example, the conventional fasteners have typically included a pair of fastening tabs, such as e.g. adhesive tape tabs, located on the outermost corners of the diaper in the back waist portion of the diaper and a complimentary fastener, such as a reception panel, located on the front waist portion. Such fastening tabs are generally manufactured separately from the articles to which they are attached. Therefore, the fastening tabs affixed to outermost corners of the diaper in the back waist portion, in a manner and with a strength sufficient to resist the forces which arise during use of the article.

A number of concepts have been introduced in the art for permanent fastening of fastening tabs to the outermost corners of the diaper such as e.g. mechanical, adhesive or ultrasonic bonding or combinations thereof.

For example, US 2007/0032766 discloses mechanical bonds to join a front side panel and a rear side panel or to join other substrates, layers and/or elements of the absorbent article, which in addition results in informational indicia.

U.S. Pat. No. 5,681,306 disclose permanent adhesive bonding between a tape tab and backsheet of the diaper.

One type of laminate produced by Koester GmbH (FlexEar PA 150 V2 EMB1) is embossed to form a number of rhomboids. This laminate may be used as elastic side panels, i.e. outermost corners of the diaper, onto which fastening tabs have been fastened.

In U.S. Pat. No. 5,605,735, a diaper comprising a stress beam section is disclosed, which may be an integral part of the side panel of the diaper or separately fastened. The section is the connection between the fastening tab and the side panel and can disperse the fastening forces across the side panel. The stress beam section may be densified or embossed to provide reliable securement.

The systems mentioned above have, however, a number of shortcomings, one of which is that the fastening tabs may come off from the outermost corners of the diaper due to the forces arising during use of the article. More specifically, the outermost corners of the diaper usually are a laminate with nonwoven on the outside surface and consequently it is difficult to get good adhesion because fibres in the nonwoven are pulled out by the adhesive between the fastening tab and the diaper or between the fastening tab and the elastic side panel.

Therefore, there remains a need for an absorbent article with improved strength and prolonged durability of the fastening between the outermost corners of the diaper and the fastening tabs of the fastening system.

SUMMARY

The disclosure provides an absorbent article including:
- a chassis extending about a longitudinal axis (L), said chassis having a transverse axis (T) dividing the absorbent article into a first body panel terminating in a first waist region and a second body panel terminating in a second waist region, said chassis being delimited by opposed longitudinal edges and opposed first and second transverse edges;
- a pair of opposed elastic side panels attached to said chassis at said second waist region of said second body panel, each elastic side panel extending outwardly from each longitudinal edge of the chassis, each elastic side panel having a proximal end portion having a proximal edge, and a distal end portion having a distal edge, wherein said proximal end portion is attached to the chassis,
- at least one fastening tab adhesively attached to said distal end portion of each elastic side panel, said at least one fastening tab having a length (l) in the transverse direction of the article and a width (w) in the longitudinal direction of the article, said distal end portion of each said elastic side panel is embossed in at least a portion thereof which is adhesively attached to the respective fastening tab, to form at least one embossed groove extending along at least 30%, preferably at least 40% and more preferably at least 60% of the width (w) of the at least one fastening tab.

More specifically, said at least one embossed groove extends along about 100% of the width (w) of the at least one fastening tab.

Suitably, said elastic side panel is embossed to form at least two, preferably at least three and more preferably at least four embossed grooves.

In one embodiment, said at least one embossed groove is substantially parallel to said distal edge of said elastic side panels.

In another embodiment, said at least one embossed groove is oblique to said distal edge of said elastic side panels.

According to another aspect, each fastening tab is attached to a portion of said distal end portion of each said elastic side panel by a low-viscosity adhesive.

According to yet another aspect, said elastic side panel is a laminate including at least one elastic film and at least one nonwoven layer.

According to yet a further aspect, said elastic side panel consists of an elastic nonwoven layer.

According to a further aspect, said proximal end portion of said elastic side panel is embossed on at least the portion thereof which is adhesively attached to the chassis, to form at least one embossed groove extending along at least 30%, preferably at least 40% and more preferably at least 60% of the width of the proximal edge of the elastic side panel.

DEFINITIONS

Permanent attachment or fastening refers to when an element has been attached to another element, and wherein the bond between the elements is relatively strong such that the elements will not generally become unjoined during normal use of the absorbent article.

The term "elastic" as used herein defines a material having a permanent elongation after relaxation of less than 10% after the material has been subjected to an elongation of at least 30% or preferably 100% in the hysteresis test. An elongation of at least 30% or 100% means an elongation to a length of at least 30% or 100% longer than the initial length of the sample.

DETAILED DESCRIPTION OF PREFERRED EMBODIMENTS

The present disclosure relates to absorbent articles, but is illustrated in the enclosed figures and the following description with reference to a diaper.

Figure 1:
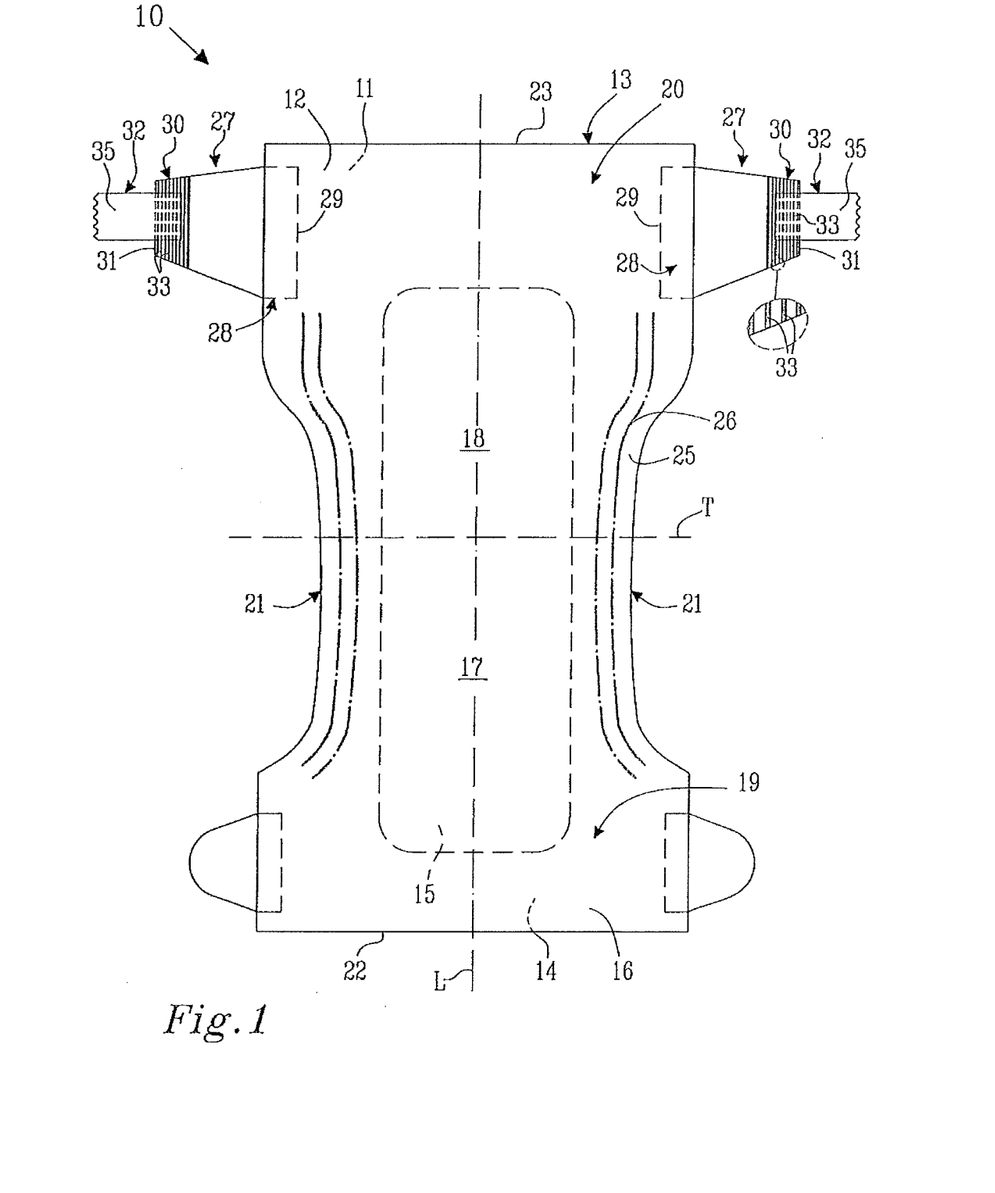
FIG. 1 shows a plan view of a diaper seen from the garment-facing side of the absorbent article according to an embodiment of the invention.

FIG. 1 shows a simplified plan view of a diaper 10 in a flat, uncontracted state seen from the garment-facing side 12. Absorbent articles 10 generally have two faces—one of which faces the body of the wearer and acts to receive exudate, referred to herein as the wearer-facing side 11, and the other of which faces the wearer's clothes, referred to herein as the garment-facing side 12. The absorbent article shown in FIG. 1 is in the form of a diaper 10 including a chassis 13 having a longitudinal axis L and a transverse T axis. The transverse axis T divides the absorbent article 10 into a first body panel 17 terminating in a first waist region 19, and a second body panel 18 terminating into a second waist region 20. Commonly, the first body panel 17 of the diaper 10 is the front body panel and the second body panel 18 is the rear body panel of the diaper 10. Moreover, between the first waist region 19 and the second waist region 20 the diaper has a crotch region 36. The diaper 10 further has opposing longitudinal edges 21, a first transverse edge 22 and a second transverse edge 23. The diaper 10 may possess longitudinal leakage barriers 24 which run substantially parallel to the longitudinal edges 21 of the diaper, which can be seen in FIG. 2. The leakage barriers 24 contain elastic and are wrinkled together at least in their centre portions.

Figure 2:
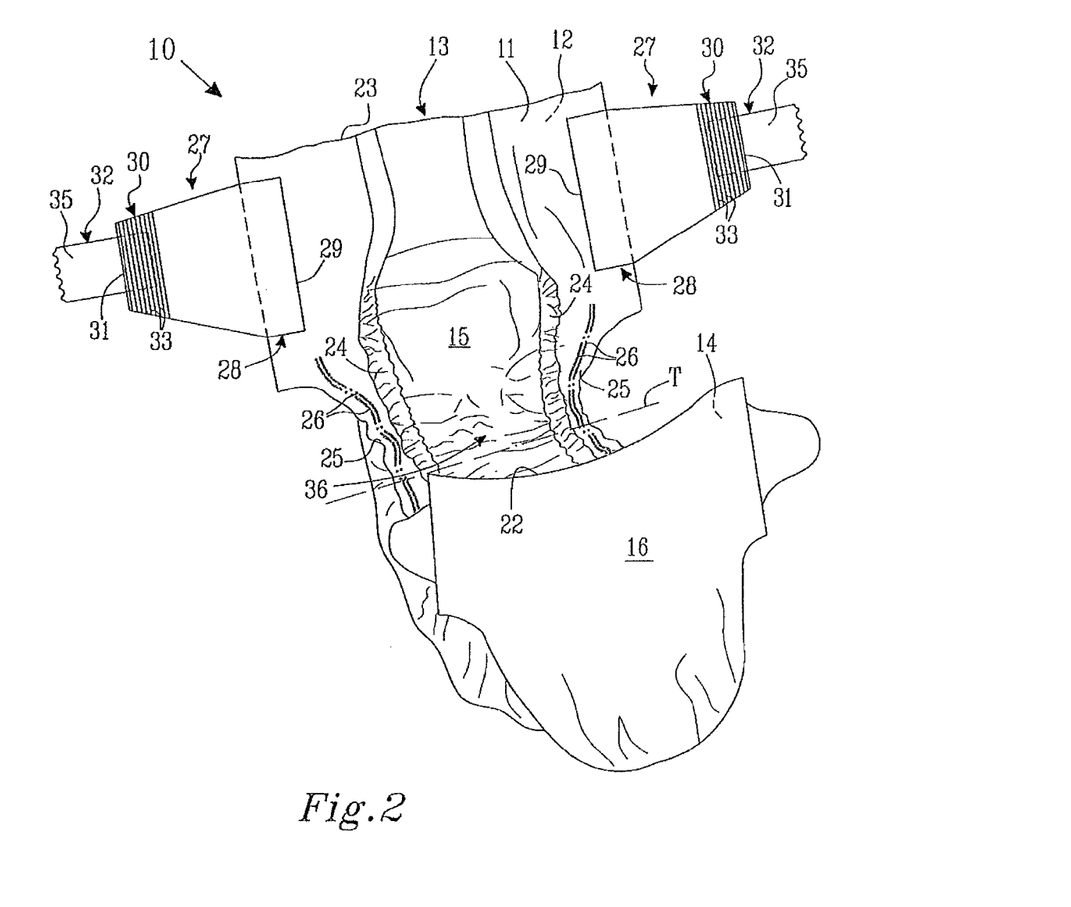
FIG. 2 shows the diaper in a contracted state seen from the wearer-facing side according to an embodiment of the invention.
Figure 3:
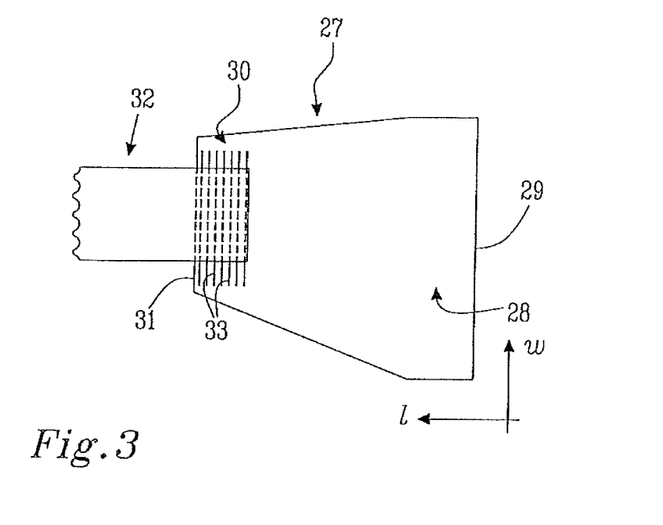
FIG. 3 shows a fastening tab attached to the elastic side panel seen from the garment-facing side of the diaper.
Figure 4A:
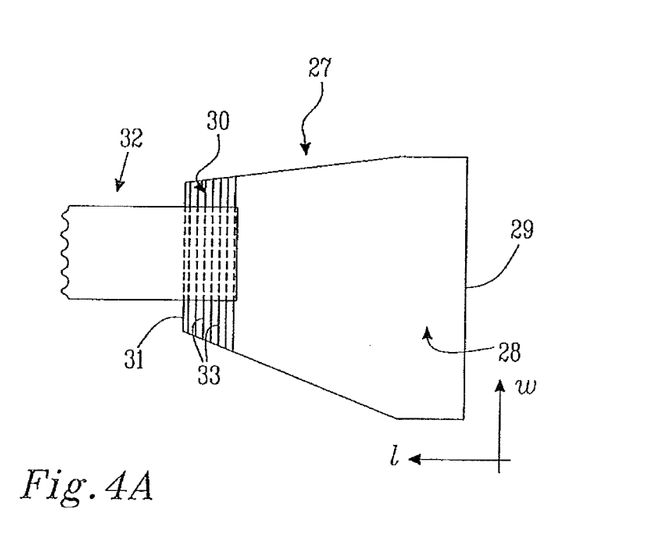
FIG. 4A shows a fastening tab attached to an elastic side panel seen from the garment-facing side of the diaper, wherein the elastic side panel is embossed to form a number of grooves that extend along more than 100% of the width of the fastening tab.
Figure 4B:
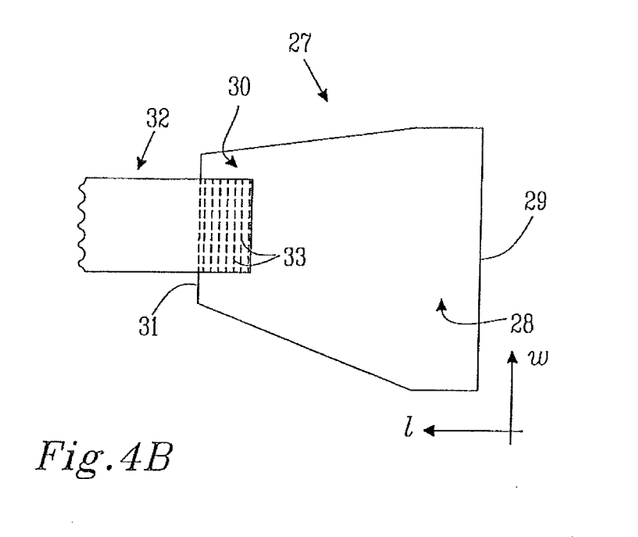
FIG. 4B shows a fastening tab attached to an elastic side panel seen from the garment-facing side of the diaper, wherein the elastic side panel is embossed to form a number of grooves that extend along about 100% of the width of the fastening tab.
Figure 4C:
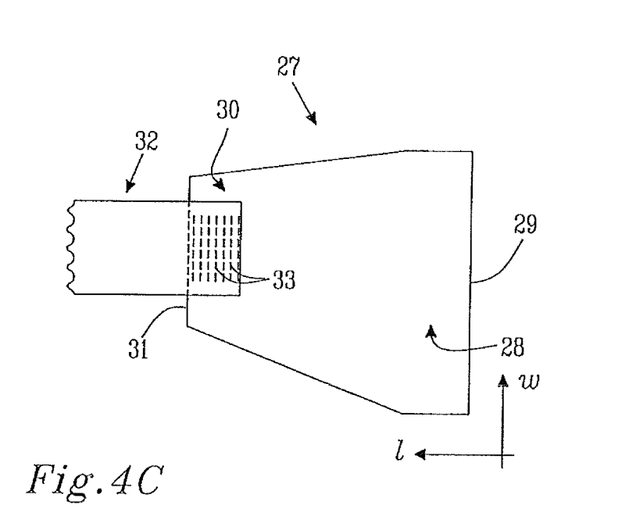
FIG. 4C shows a fastening tab attached to an elastic side panel seen from the garment-facing side of the diaper, wherein the elastic side panel is embossed to form a number of grooves that extend along about 60% of the width of the fastening tab.

Side flaps 25 extend at the sides outside the leakage barriers 24 and possess at least one longitudinal elastic element 26 in the crotch region 36 along their free edges, see FIG. 2. Upon use of the article the elastic elements 26 serve as leg elastic and provide an extra leakage barrier.

Usually, absorbent articles 10 include a liquid permeable topsheet 14, a liquid impermeable backsheet 16 and an absorbent core 15 disposed therebetween. However, articles that do not include a liquid permeable topsheet 14, a liquid impermeable backsheet 16 and an absorbent core 15 disposed therebetween are also intended to be included within the scope of embodiments of the invention.

The liquid-permeable topsheet 14 in use is placed in direct contact with the skin of the wearer and is the inner coversheet on the wearer-facing side 11 of the diaper 10. The topsheet 14 can include a nonwoven material, e.g. spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and man-made fibres. The topsheet material may further be composed of tow fibres, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and be readily penetrated by body fluid, e.g. urine or menstrual fluid. The topsheet 14 may further be different in different parts of the diaper 10.

The liquid-impervious backsheet 16 is the outer coversheet on the garment-facing side 12 of the diaper 10 and can comprise or consist of a liquid-impermeable plastic film, e.g. a polyethylene or polypropylene film, a nonwoven sheet treated with liquid-resistant material, or some other flexible material layer which has the ability to resist liquid penetration. It is usually an advantage if the liquid-impermeable backsheet 16 is breathable, i.e. allows the passage of water vapour through the sheet 16. Examples of breathable backsheet materials are porous polymeric films, nonwoven laminates of spunbond and meltblown layers and laminates of porous polymeric films and nonwoven materials. In particular embodiments, the backsheet 16 includes nonwoven material in at least the garment-facing surface thereof.

The absorbent core 15 is the absorbent structure disposed between the topsheet 14 and the backsheet 16 of the diaper 10. The absorbent core 15 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent structure. Superabsorbent polymers are water-swellable, water-insoluble organic or inorganic materials capable of absorbing at least about 20 times their own weight of an aqueous solution containing 0.9 weight percent of sodium chloride. Organic materials suitable for use as superabsorbent materials can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers can be lightly cross-linked to render the material substantially water insoluble. Particular superabsorbent materials are further surface cross-linked so that the outer surface or shell of the superabsorbent particle, fibre, flake, sphere, etc. possesses a higher crosslink density than the inner portion of the superabsorbent. The superabsorbent materials may be in any form which is suitable for use in absorbent composites including particles, fibres, flakes, spheres, and the like.

The absorbent core 15 may also be constructed of more than one layer of absorbent material. Absorbent structures usually contain layers of wadding—so-called receiving and distribution layers—to be able to rapidly take away released liquid from the liquid-permeable topsheet 14. Each of the layers including the absorbent core 15 may naturally contain superabsorbents.

The topsheet 14 and the backsheet 16 extend outwardly beyond the peripheral edges of the absorbent core 15 and have their inner surfaces bonded to each other, e.g. by gluing or welding by heat or ultrasonic. The topsheet 14 and backsheet 16 materials may further be bonded, e.g. by adhesive, to the absorbent core 15.

As seen in FIGS. 1 and 2, the second body panel 18 is provided with opposing elastic side panels 27 and at least one fastening tab 32, including fasteners 35, attached thereto. The opposed elastic side panels 27 are attached to the chassis 13 at the second waist region 20 of the second body panel 18. In FIGS. 1-7 it is shown that each elastic side panel 27 extends outwardly from each distal edges of the chassis 13. In one embodiment, the elastic side panels 27 are a separate element, which is attached to the backsheet 16 of the diaper 10. In another embodiment, the elastic side panels 27 are a continuation of the backsheet 16. Each elastic side panel 27 has a proximal end portion 28 with a proximal edge 29 attached to the chassis 13. Further, each elastic side panel 27 has a distal end portion 30 with a distal edge 31. In addition, the distal and proximal edges of the elastic side panel 27 have a width (w) in the longitudinal direction of the diaper 10. Each elastic side panel 27 is adhesively fastened to at least one fastening tab 32 as mentioned above. In one embodiment, of the present invention the at least one fastening tab 32 may extend outwardly from each distal edge 31 of the elastic side panel 27, see FIGS. 1-7. In a further embodiment, the at least one fastening tab 32 does not extend outwardly from the distal edge 31 of each elastic side panel 27, but the entire at least one fastening tab 32 is fastened to the elastic side panel 27. The at least one fastening tab 32 has a length (l) in the transverse direction of the article 10 and a width (w) in the longitudinal direction of the diaper 10, see FIG. 3-4. The at least one fastening tab 32 also has opposing upper and lower edges. The fasteners 35 on the at least one fastening tab 32 are intended to be fastened to the first body panel 17 of the article 10 to form a pant-like shape during use. The fasteners 35 may be in the form of adhesive tapes or hook elements adapted to attach to a loop material, for example in the form of a nonwoven material forming the backsheet 16 of the diaper 10.

Typically, the distal end portion 30 of each elastic side panel 27 is adhesively attached to at least one fastening tab 32 as mentioned above. To improve the attachment between each elastic side panel 27 and the at least one fastening tab 32, the distal end portion 30 of each elastic side panel 27 is embossed to form at least one groove 33 that extends along at least 30%, preferably at least 40% and more preferably at least 60% of the width (w) of the at least one fastening tab 32, see FIGS. 1-7 and more specifically FIG. 4C. The at least one groove 33 may also extend 100% of the width (w) of the at least one fastening tab 32, see FIGS. 4A and 4B. For example, each elastic side panel 27 is embossed to form at least one groove 33 that extends along at least 1 cm, preferably at least 2 cm and more preferably at least 3 cm of the width (w) of the at least one fastening tab 32. The presence of the at least one embossed groove 33 in the elastic side panel 27 further results in that the elasticity of the elastic side panel 27 is preserved.

The at least one fastening tab 32 may take any shape. In one embodiment, the at least one fastening tab 32 may have a smaller width (w) than the width (w) of the distal edge 31 of the elastic side panel 27. The at least one fastening tab 32 may then be centred or placed in alignment with the upper or lower edge of the elastic side panel 27. In one embodiment, the at least one fastening tab 32 has substantially the same width (w) as the width (w) of the distal edge 31 and consequently the tab 32 is placed substantially in alignment with the upper and lower edge of the elastic side panel 27.

Figure 5A:
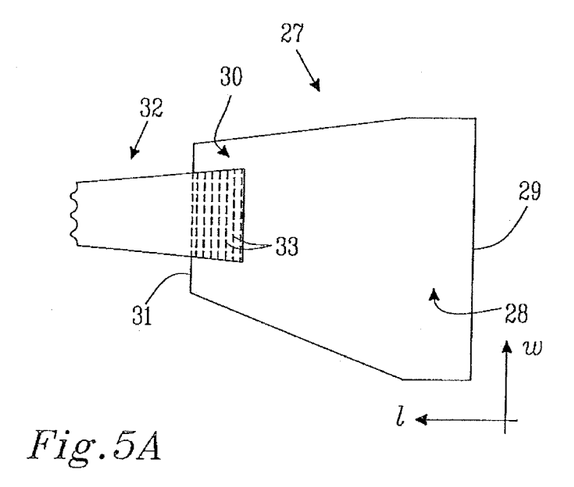
FIGS. 5A and 5B shows examples of fastening tabs with oblique upper and lower edges.
Figure 5B:
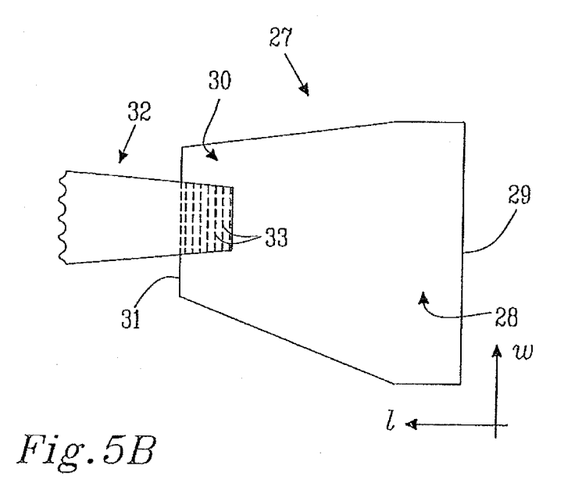
Figure 6A:
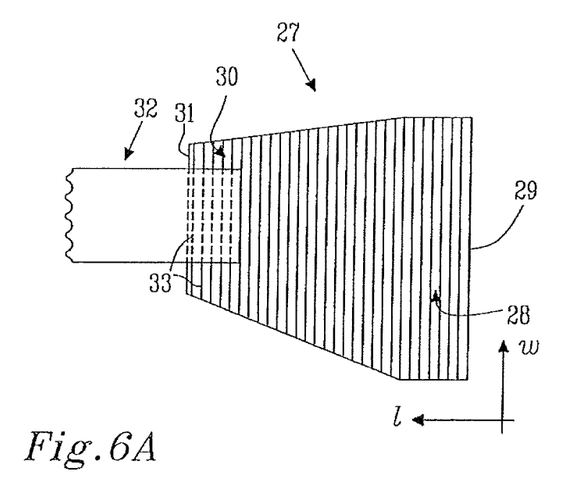
FIG. 6A shows a fastening tab attached to an elastic side panel seen from the garment-facing side of the diaper, wherein the entire elastic side panel is embossed to form a plurality of grooves.
Figure 6B:
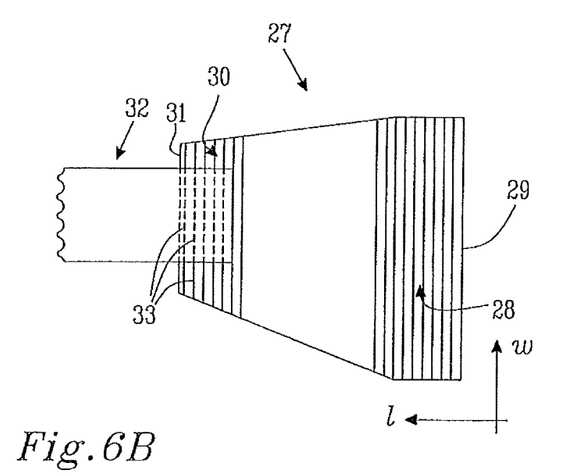
FIG. 6B shows a fastening tab attached to an elastic side panel seen from the garment-facing side of the diaper, wherein the proximal end portion and the distal end portion of the elastic side panel is embossed to form a plurality of grooves.

In FIGS. 5A and 5B it is disclosed that the at least one fastening tab 32 may have oblique upper and/or lower edges, and the width (w) of the at least one fastening tab 32 thus varies. The width (w) of the at least one fastening tab 32 is then defined as maximum width (w) of the at least one fastening tab 32 adhesively attached to the distal end portion 30 of the elastic side panel 27.

The at least one groove 33 can be an embossed furrow which extends along at least 30%, preferably at least 40% and more preferably at least 60% of the width (w) of the at least one fastening tab 32 as mentioned above. In one embodiment, if there is a plurality of grooves, all the grooves 33 in the elastic side panel 27 have the same extension along the width (w) of the at least one fastening tab 32. In another embodiment, at least some of the grooves 33 may have varying extension along the width (w) of the at least one fastening tab 32. In a further embodiment, at least some of the embossed grooves 33, which may have the same extension along the width (w) of the at least one fastening tab 32 or which may have different extension along the width (w) of the at least one fastening tab 32, may be displaced vertically relative each other. By vertically in this context it is meant when the diaper is in use.

Figure 7:
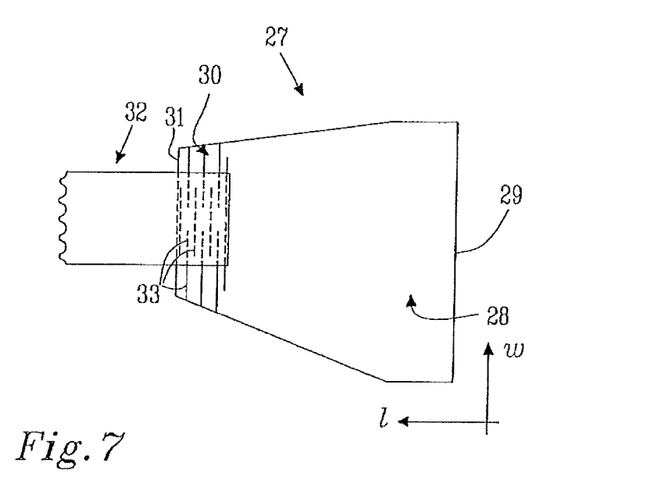
FIG. 7 shows a fastening tab attached to an elastic side panel seen from the garment-facing side of the diaper, wherein a plurality of embossed grooves are displaced vertically relative each other, and wherein a plurality of embossed grooves are colinear.

In yet another embodiment, some of the plurality of embossed grooves on each elastic side panel 27 may be embossed colinear, see FIG. 7. For example, two or three embossed grooves 33 may be colinear along the width (w) of the at least one fastening tab 32. In addition, it may be possible to combine at least one embossed groove 33 with other embossed grooves.

If there is a plurality of embossed grooves 33, each embossed groove 33 may have different extension along the length (l) of the at least one fastening tab 32. Thus, some grooves 33 may be thinner and some grooves may be thicker than each other. Each of the at least one embossed grooves 33 may also extend variably in its width along the length (l) of the at least one fastening tab 32. The width-length relationship of the at least one groove is suitably between 1:5 and 1:650, and preferably 1:10 and 1:350.

In one embodiment, each elastic side panel 27 is embossed to form at least one groove 33 on the garment-facing side 12 of the diaper 10 onto which the at least one fastening tab 32 is attached. However, each elastic side panel 27 may be embossed to form grooves 33 on the garment-facing side 12 as well as on the wearer-facing side 11.

Each elastic side panel 27 may be embossed to form at least two, preferably at least three and more preferably at least four embossed grooves 33. Each elastic side panel 27 does not need to include the same number of grooves 33.

There are different ways of forming the embossed grooves 33. For example, the grooves 33 may be imprinted or stamped to enable the tachability of the elastic film.

Figure 8:
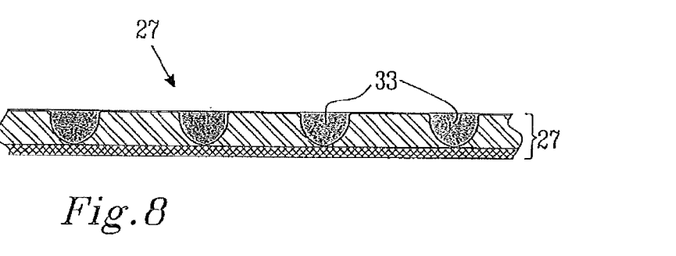
FIG. 8 shows a schematic picture of a cross section of the elastic side panel which is embossed to form a number of grooves.

When the nonwoven layer is embossed, the fibres may be compressed such that the elastic or non-elastic film of the laminate is reached, see FIG. 8. In one embodiment, the plurality of grooves 33 has different depth such that some grooves 33 reach the film and some grooves 33 do not. The fiber ends of the nonwoven layer are however directed downwards and flattened independently of whether they reach the film or not. In another embodiment, the plurality of grooves 33 has the same depth and all grooves 33 reach the film.

The at least one embossed groove 33 may be of any shape as long as it extends along at least 30%, preferably at least 40% and more preferably at least 60% of the width (w) of the at least one fastening tab 32. The at least one embossed groove 33 may be parallel or oblique, e.g. diagonal, to the distal edge 31 of the elastic side panel 27. Further, the at least one groove 33 may be e.g. half moon shaped, zigzag shaped, wave shaped or sinusoidal curve shaped. If there is a plurality of embossed grooves 33, some or all of the embossed grooves 33 may intersect.

The plurality of grooves 33 may be embossed with the same distance between the individual grooves 33 along the length (l) of the at least one fastening tab 32. Possibly, the distance between the individual embossed grooves 33 may vary along the length (l) of the at least one fastening tab 32.

In a particular embodiment, the at least one fastening tab 27 is attached to the distal end portion 30 of each elastic side panel 27 by a low-viscosity adhesive. The viscosity of the adhesive at 175° C. may be about 8000 to 20 000 mPas, preferably about 10 000 to 18 000 mPas and more preferably about 12 000 to 16 000 mPas. A number of different adhesives can be used, e.g. Fueller HL 1696. The low-viscosity adhesive is distributed in the grooves 33 along the width (w) of the at least one fastening tab 32 and thereby covering a greater part of the elastic side panel 27. The at least one fastening tab 32 and the adhesive also has a better possibility to reach the elastic film in the grooves 33. As a result, the attachment between the elastic side panel and the at least one fastening tab 32 has an improved shear force as shown in the experimental section below in Table 1.

In a particular embodiment, the elastic side panels 27 are a laminate. The elastic laminate may be a laminate between two or more nonwoven layers, two or more film layers or a combination of film and nonwoven layers. Thus, the elastic side panel 27 may include a non-elastic nonwoven and an elastic film or a non-elastic nonwoven, an elastic film and a non-elastic nonwoven. Possibly, the elastic side panel 27 is not a laminate but the elastic side panel 27 consists of an elastic nonwoven layer only. Moreover, the elastic side panel may be elastic in at least the transverse direction of the diaper 10, however it may also be elastic in the longitudinal direction. In the embodiment where the elastic side panel 27 consists of an elastic nonwoven, the adhesive reaches the bottom of the at least one groove 33, where the nonwoven fibres have been flattened and melted due to embossment, and is efficiently bonded and distributed.

Each elastic side panel 27 may, in addition to being embossed to form grooves 33 at the distal end portion 30 of the elastic side panel 27, also be embossed to form grooves 33 at other locations of the elastic side panel 27. In one embodiment, the entire elastic side panel 27 may be embossed to form grooves 33, see FIG. 6A and in another embodiment only the distal end portion 30 and the proximal end portion 28 of each elastic side panel 27 may be embossed to form grooves 33, see FIG. 6B. For example, the proximal end portion 28 of the elastic side panel 27 may also be embossed to form grooves 33 extending along at least 30%, preferably at least 40% and more preferably at least 60% of the width of the proximal edge 29 of the elastic side panel 27, to improve the adhesive attachment of each elastic side panel to the chassis 13 in the same way as the at least one fastening tab 32 to the elastic side panel 27.

Although the invention has been described with reference to a number of embodiments and Figures, it should not be considered as being limited thereto. In particular, the invention is equally applicable to absorbent articles other than diapers, such as, incontinence guards, sanitary napkins and panty liners. Variations of materials, components, elements and their locations will be readily understood by persons skilled in the art. The scope of protection should therefore be defined by the enclosed claims.

EXPERIMENTAL SECTION

In the test performed below, a number of products of each sample have been tested, such that average measures may be computed for each sample. However, it is understood that if it is necessary to determine any measure for one single sample, the test methods are applicable although it is not necessary to form a mean value.

Samples
  Reference:
  A laminate, including an elastic film and a nonwoven layer on each side of the film, which is partly embossed to form a number of rhomboids, is used as elastic side panel.
  Product According to the Disclosure:
  A laminate, including an elastic film and a nonwoven layer on each side of the film, which is partly embossed to form a plurality of grooves, is used as elastic side panel.
  In each case (reference and product according to the disclosure), the same laminate was used for comparison purposes.
  At least one fastening tab is attached to each of the elastic side panels of the samples mentioned above by means of an adhesive. Approximately, 40-100 gsm (grammage per square meters) of adhesive is used to attach the tab onto the elastic side panel.

Figure 9:
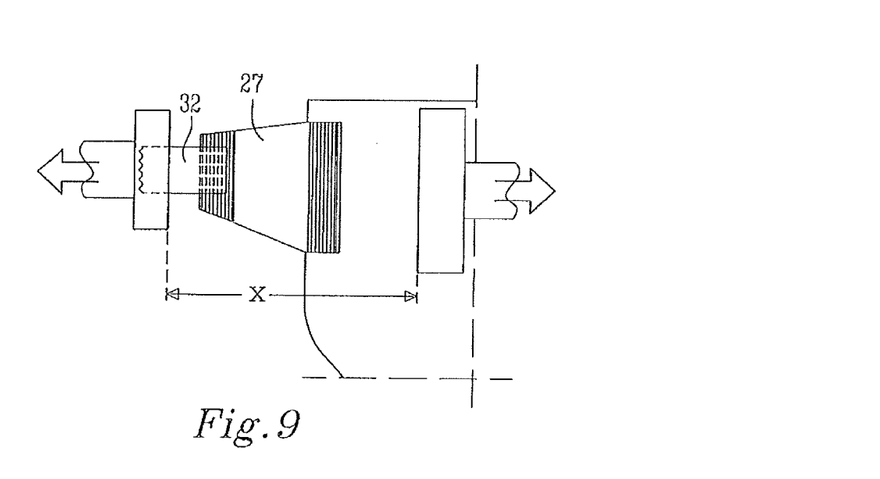
FIG. 9 shows a schematic picture of how the Dynamic shear force test is performed.

Dynamic Shear Test
  Aim:
  The aim of the Dynamic shear test is to determine the force required to separate the fastening tab from the elastic side panel. This is done by measuring the max load by means of a tensile tester.
  Test Procedure:
  As illustrated in FIG. 9 the Dynamic shear test is performed by marking the required clamp distance (x) on the product. It is possible to test one joining or several joints at the same time. If a joint is wider than 120 mm, note this in the result. Mark right and left side. Calibrate and zero the tensile tester on the specific clamp distance. Fasten the sample in the tensile tester. Try to get the tab or the elastic side panel as centered as possible. Do not fasten the sample slanting. Start the tensile tester. Stop when the fastening tab is totally released from the underlying material. Note the value for the max force in N. Note the order in which the materials have broken. If the absorbent structure is affecting the results, causing gliding in the clamps e.g., remove the pulp.

Figure 10:
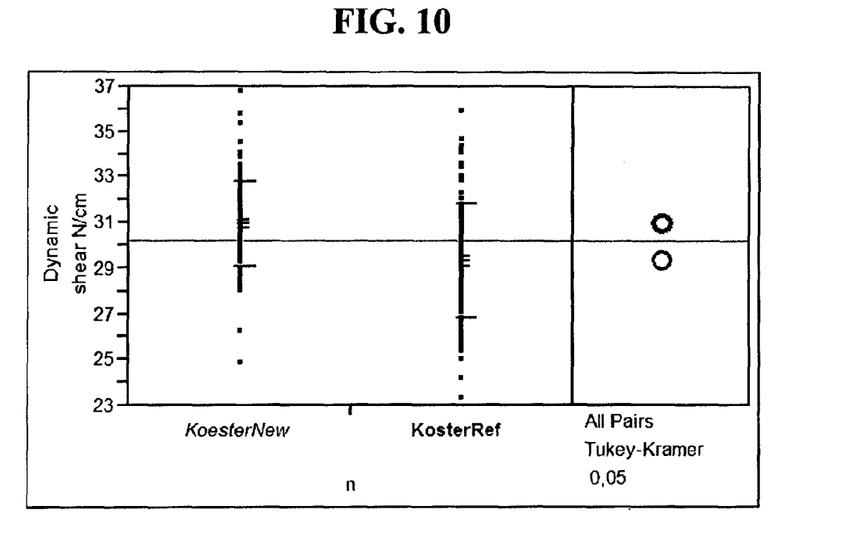
FIG. 10 show the results of the Dynamic shear force test.

Apparatus:
Tensile tester connected to a computer
Crosshead speed: 300 mm/min
Cell: 100 N
Clamp width: 50 mm or 120 mm wide upper clamp, 120 mm wide lower clamp.
x=clamp distance The results of the Dynamic shear force test that are represented in FIG. 10.

Discussion:

When the results for the different tested samples shown in Table 1 are compared, it is realized that there is a significant difference between the samples according to the disclosure and the reference samples. The dynamic shear test shows that a higher mean force (N/cm) is needed in order to separate the fastening tab from the elastic side panel of the samples according to the disclosure compared to the reference samples.

The invention claimed is:

1. An absorbent article comprising:
 a chassis extending about a longitudinal axis, said chassis having a transverse axis dividing the absorbent article into a first body panel terminating in a first waist region and a second body panel terminating in a second waist region, said chassis being delimited by opposed longitudinal edges and opposed first and second transverse edges;
 a pair of opposed elastic side panels attached to said chassis at said second waist region of said second body panel, each of said elastic side panels extending outwardly from each longitudinal edge of the chassis, each of said elastic side panels having a proximal end portion having a proximal edge and a distal end portion having a distal edge, wherein said proximal end portion is attached to the chassis; and
 at least one fastening tab attached to said distal end portion of each of said elastic side panels by an adhesive, said at least one fastening tab having a length in the transverse direction of the article and a width in the longitudinal direction of the article,
 wherein said distal end portion of each of said elastic side panels includes a plurality of grooves that are substantially parallel to each other and extend in the longitudinal direction of the article along the entire width of the at least one fastening tab, the grooves of each of said elastic side panels being filled with the adhesive, the adhesive forming a body inside the grooves that provides for a bond between the respective side panel and fastening tab.

2. The absorbent article according to claim 1, wherein said plurality of grooves extend to about 100% of the width of the at least one fastening tab.

3. The absorbent article according to claim 1, wherein at least one of said elastic side panels is a laminate comprising at least one elastic film and at least one nonwoven layer.

4. The absorbent article according to claim 1, wherein at least one of said elastic side panels consists of an elastic nonwoven layer.

5. The absorbent article according to claim 1, wherein said proximal end portion of at least one of said elastic side panels includes the plurality of grooves on at least the portion thereof which is adhesively attached to the chassis, the grooves extending along at least 30% of the width of the proximal edge of the elastic side panel.

6. The absorbent article according to claim 1, wherein the plurality of grooves have a semi-circular cross-sectional shape.

7. The absorbent article according to claim 1, wherein the plurality of grooves extend into an area of the elastic side panels that is located adjacent to the fastening tab in the longitudinal direction of the article.

8. The absorbent article according to claim 1, wherein the plurality of grooves are continuous in the longitudinal direction of the article along the respective elastic side panels.

9. The absorbent article according to claim 1, wherein the grooves are substantially parallel to said distal edge of the elastic side panel.

* * * * *